US00PP18218P2

(12) United States Plant Patent
Sanders

(10) Patent No.: US PP18,218 P2
(45) Date of Patent: Nov. 13, 2007

(54) **NEW GUINEA *IMPATIENS* PLANT NAMED 'INGBRISAL'**

(50) Latin Name: *Impatiens hawkeri*
Varietal Denomination: Ingbrisal

(75) Inventor: Monica Maria Adelheid Sanders, Grootebroek (NL)

(73) Assignee: Syngenta Seeds B.V., Enkhuizen (NL)

( * ) Notice: Subject to any disclaimer, the term of this patent is extended or adjusted under 35 U.S.C. 154(b) by 0 days.

(21) Appl. No.: 11/437,937

(22) Filed: May 19, 2006

(51) Int. Cl.
*A01H 5/00* (2006.01)

(52) U.S. Cl. ..... Plt./318
(58) Field of Classification Search ..... Plt./318
See application file for complete search history.

(56) References Cited

U.S. PATENT DOCUMENTS

PP14,812 P2 * 5/2004 Hofmann ..... Plt./318
PP16,194 P2 * 1/2006 Kientzler ..... Plt./318

OTHER PUBLICATIONS

UPOV ROM GTITM Computer Database, GTI Retrieval Software 2006/04.*

* cited by examiner

*Primary Examiner*—Wendy C. Haas
(74) *Attorney, Agent, or Firm*—Bruce Vrana

(57) ABSTRACT

A new and distinct cultivar of New Guinea *Impatiens* plant named 'Ingbrisal' characterized by its large white colored flowers with broad salmon edge with medium large, dark green foliage, early flowering, good heat tolerance, nice rounded shaped growth habit with excellent basal branching and good vigor.

1 Drawing Sheet

Latin name of the genus and species of the plant claimed: *Impatiens hawkeri.*
Varietal denomination: 'Ingbrisal'.

BACKGROUND OF THE NEW PLANT

The present invention comprises a new and distinct New Guinea *Impatiens* plant botanically known as *Impatiens hawkeri* and referred to by the cultivar name 'Ingbrisal.'

The new cultivar was developed in a controlled breeding program conducted by the inventor in Enkhuizen, Netherlands. The new New Guinea *Impatiens* cultivar is very floriferous with large flowers, early flowering on a strong growing, basal branching plant with good heat tolerance.

The new cultivar is propagated from cuttings resulting from the cross in September 2001 of the proprietary New Guinea *Impatiens* selection identified as 'MM154-1' as female parent and the proprietary New Guinea *Impatiens* selection identified as 'H267-7' as male parent. 'MM154-1' is not commercially available and has not been patented. 'H267-7' is not commercially available and has not been patented.

As a result of this cross the present cultivar was selected as a single plant in September 2002 in Enkhuizen, Netherlands and has been repeatedly asexually reproduced by cuttings in Enkhuizen, Netherlands, in Gilroy, Calif., and in Angers, France over a period of several years. The distinctive characteristics of this new *Impatiens* are stable and reproduced true to type in successive generations of asexual reproduction. It takes 9 to 10 weeks to produce a finished plant, starting from a rooted plug and planted in a 12 cm pot, depending on the temperature.

SUMMARY OF THE INVENTION

The following traits have been repeatedly observed and are determined to be the unique characteristics of 'Ingbrisal.'

These characteristics in combination distinguish 'Ingbrisal' as a new and distinct New Guinea *Impatiens* cultivar:

1. Large white flowers with broad salmon edge
2. Early flowering and floriferous habit
3. Rounded shaped habit
4. Strong growing and good heat tolerance Plants of the new New Guinea *Impatiens* differ primarily from the plants of the female parent selection in the following characteristic:

Plants of the New Guinea *Impatiens* have white colored flowers with broad salmon edge, whereas the plants of the female parent selection have pink blush colored flowers.

Plants of the new New Guinea *Impatiens* differ primarily from the plants of the male parent selection in the following characteristic:

Plants of the New Guinea *Impatiens* have white colored flowers with broad salmon edge, whereas the plants of the male parent selection have light pink colored flowers.

Plants of the new New Guinea *Impatiens* can be compared to plants of 'Fisnics Salmon Ice,' U.S. Plant Pat. No. 14,812. In side-by-side comparisons conducted in Enkhuizen, Netherlands, plants of the new New Guinea *Impatiens* differed from plants of the cultivar 'Fisnics Salmon Ice' in the following characteristics:

1. Plants of the new New Guinea *Impatiens* have large white flowers with broad salmon edge, whereas plants of 'Fisnics Salmon Ice' have medium large light salmon flowers with big white spot.
2. Plants of the new New Guinea *Impatiens* have dark green foliage, whereas plants of 'Fisnics Salmon Ice' have green foliage.

DESCRIPTION OF THE DRAWING

This new New Guinea *Impatiens* plant is illustrated by the accompanying photographic drawing which shows blooms, buds and foliage of the plant in full color, the color showing being as true as can be reasonably obtained by conventional photographic procedures.

DESCRIPTION OF THE NEW CULTIVAR

The following detailed descriptions set forth the distinctive characteristics of this new New Guinea *Impatiens*. The data which defines these characteristics were collected from asexual reproductions carried out in Enkhuizen, Netherlands. The plant history was taken on 30 week old plants, blossomed under natural light in the field.

Color readings were taken in the laboratory under ambient light. Color references are primarily to The R.H.S. Color Chart of The Royal Horticultural Society of London.

The plant:
- *Classification.*—Botanical: *Impatiens hawkeri.*

Parentage:
- *Female parent.*—Proprietary *Impatiens hawkeri* selection identified as code number 'MM154-1,' not patented.
- *Male parent.*—Proprietary *Impatiens hawkeri* selection identified as code number 'H267-7,' not patented.

Propagation:
- *Type cutting.*—Terminal cuttings.
- *Time to initiate roots.*—Approximately 7–14 days.
- *Time to produce a rooted cutting.*—Approximately 21 days.
- *Root description.*—Fine, fibrous, and white in color.

Plant description:
- *General appearance.*—Outwardly spreading, low rounded and uniform mounded plant growth.

Habit:
- *Growth and branching habit.*—Freely branching habit, freely flowering, vigorous.

Crop time:
- *Plant height.*—24–26 cm.
- *Plant spread.*—35–40 cm.

Lateral branch description:
- *Length:* 10–15 cm.
- *Diameter.*—4–6 mm.
- *Texture.*—Smooth, glabrous.
- *Internode length.*—2–7 cm.
- *Color.*—RHS 187A.

Foliage description:
- *Arrangement.*—Primarily in whorls.
- *Length, mature leaves.*—7.4 cm.
- *Width, mature leaves.*—2.7 cm.
- *Shape.*—Lanceolate.
- *Apex.*—Acuminate.
- *Base.*—Acute.
- *Margin.*—Serrulate with fine cilation.
- *Texture.*—Smooth, glabrous.
- *Venation pattern.*—Pinnate.
- *Color young foliage, upper surface.*—RHS 146A.
- *Color young foliage, lower surface.*—RHS 187B.
- *Fully expanded foliage, upper surface.*—RHS 147A.
- *Fully expanded foliage, lower surface.*—RHS 187C.
- *Venation, upper surface.*—RHS 187B.
- *Venation, lower surface.*—RHS 187A.
- *Anthocyanin may be present.*—RHS 187B.
- *Petiole length.*—About 0.6 cm.
- *Petiole diameter.*—About 3 mm.
- *Texture.*—Smooth, glabrous.
- *Color.*—RHS 187B.

Flower description:
- *Flower type and flowering habit.*—Single.
- *Number of flowers per leaf axil.*—1 or 2.
- *Number of flowers and flower buds per lateral branch.*—5.
- *Flower position.*—Above and beyond the foliage and typically facing upwards and outward.
- *Flower shape.*—Rounded, mostly flat.
- *Flowers lasting.*—About 10 days on the plant depending on environmental conditions.
- *Petals.*—Self cleaning.
- *Gynoecium.*—Persistent.
- *Flowers.*—Not fragrant.
- *Flowering.*—Indeterminate and continuous.
- *Flowering season.*—Year round under greenhouse conditions. In the garden, flowering from spring until fall.
- *Flower length.*—About 7.0 cm.
- *Flower width.*—About 7.1 cm.
- *Flower depth.*—About 1 cm.

Flower buds:
- *Bud length.*—About 2 cm.
- *Bud diameter.*—About 1.6 cm.
- *Bud shape.*—Ellipsoidal.
- *Texture.*—Smooth, glabrous.
- *Color, just before opening.*—RHS 52B.

Petals:
- *Quantity.*—Single, five per flower, imbricate.
- *Length of banner petal.*—About 3.0 cm.
- *Width of banner petal.*—About 5 cm.
- *Length lateral and basal petals.*—About 4 cm.
- *Width lateral and basal petals.*—About 4 cm.
- *Lateral and basal petal shape.*—Cordate.
- *Banner petal shape.*—Roughly cordate.
- *Petal apex.*—Retuse to emarginate.
- *Petal base.*—Attenuate.
- *Petal margin.*—Entire.
- *Petal texture.*—Smooth, satiny.
- *Petal color.*—Upper surface: When opening and fully opened: RHS 52C Middle: N155C with blotch 67B. Lower surface: When opening and fully opened: RHS 52D.

Spur:
- *Length.*—About 4.9 cm.
- *Texture.*—Smooth, glabrous.
- *Aspect.*—Curved.
- *Color.*—RHS 53A.

Peduncles:
- *Length.*—About 5 cm.
- *Strength.*—Strong, flexible.
- *Diameter.*—0.15 cm.
- *Aspect.*—About 45° from the stem.
- *Color.*—RHS 53A.

Reproductive organs:
- *Androecium.*—Stamen number: Five fused at anthers, filaments free, hooded.
- *Anther shape.*—Obovate.
- *Anther length.*—About 6 mm.
- *Anther color.*—RHS 161C to 53B.
- *Amount of pollen.*—Abundant.
- *Pollen color.*—RHS 4D.

Gynoecium:
- *Pistil number.*—One.
- *Pistil length.*—About 4 mm.
- *Stigma shape.*—Columnar, five segmented.
- *Stigma color.*—Colorless.

*Style color.*—RHS 183A.

*Ovary arrangement.*—Five celled.

*Ovary color.*—RHS 144A.

Seed development: Seed development has not been observed.

Disease and pest resistance: Resistance to pathogens and pests common to *Impatiens* has not been observed.

What is claimed is:

1. A new and distinct cultivar of New Guinea *Impatiens* plant named 'Ingbrisal', as substantially illustrated and described herein.

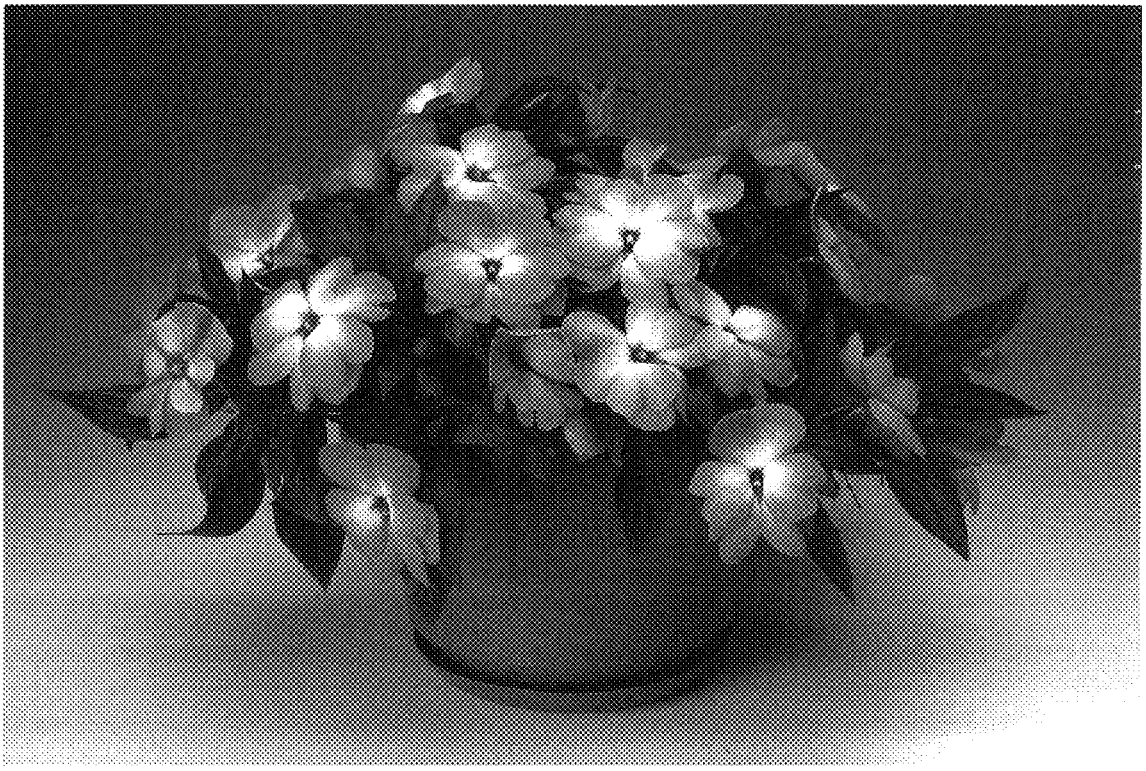

* * * * *